United States Patent
Umio et al.

[11] 3,965,122
[45] June 22, 1976

[54] CHROMONE COMPOUNDS AND PREPARATION THEREOF

[75] Inventors: Suminori Umio, Kawanish; Shizuo Maeno, Osaka; Ikuo Ueda, Yao; Yoshinari Sato, Takaishi; Masaaki Matsuo, Toyonaka, all of Japan

[73] Assignee: Fujisawa Pharmaceutical Co., Ltd., Osaka, Japan

[22] Filed: Dec. 28, 1971

[21] Appl. No.: 213,180

[30] Foreign Application Priority Data
Dec. 30, 1970 Japan.............................. 45-129469
Dec. 30, 1970 Japan.............................. 45-129470

[52] U.S. Cl............................ 260/345.2; 424/283; 260/332.3 P; 260/297 B

[51] Int. Cl.²................................... C07D 311/28
[58] Field of Search........................ 260/345.2, 345.5

[56] References Cited
UNITED STATES PATENTS

3,419,578   12/1968   Fitzmaurice et al............. 260/345.2
3,862,175   1/1975    Fitzmaurice et al............. 260/345.2

*Primary Examiner*—John M. Ford
*Attorney, Agent, or Firm*—Bierman & Bierman

[57] ABSTRACT

Chromone compounds having the structure

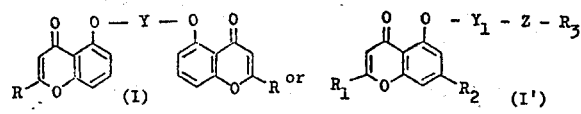

wherein R is aryl, substituted aryl, thienyl, furyl or pyridyl, Y is hydroxy(lower)alkylene, $R_1$ is hydrogen, lower alkyl, aryl, substituted aryl or a heterocyclic group, $R_2$ is hydrogen or lower alkoxy, $Y_1$ is lower alkylene or hydroxyl(lower)alkylene, Z is oxygen or sulfur and $R_3$ is hydrogen, lower alkyl, aryl, substituted aryl, or ar(lower)alkyl have anti-allergic activity and are useful in the treatment of asthma. Compounds of the structure [I] are prepared by reacting

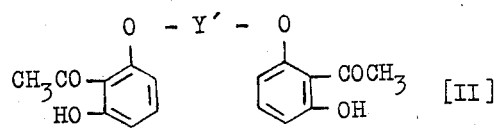

wherein Y' is hydroxy(lower)alkylene whose hydroxy group is optimally protected or a reactive derivative of [II] with a carboxylic acid of the formula R—COOH in the presence of a basic catalyst. The resulting compound is then reacted with an acid. Compounds of the structure [I'] are prepared by reacting the compound

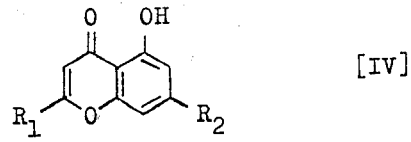

with the compound $X-Y'_1-Z-R'_3$ wherein X is an acid residue, Y' is lower alkylene or hydroxy(lower)alkylene whose hydroxy group is optionally protected by a protective group, $R'_3$ is hydrogen, lower alkyl, aryl, substituted aryl, or ar(lower)alkyl and Z is as defined above. When $R'_3$ is hydrogen, $-Z-R'_3$ is optionally protected by a protective group. The resultant compound is subjected to an elimination reaction when Y' is a protected group or when $-Z-R'_3$ is protected to split off the protective group.

8 Claims, No Drawings

CHROMONE COMPOUNDS AND PREPARATION THEREOF

This invention relates to new chromone compounds which possess an anti-allergic activity, process for preparing the same and a composition thereof.

The chromone compounds can be represented by a member selected from the group consisting of the following general formulae:

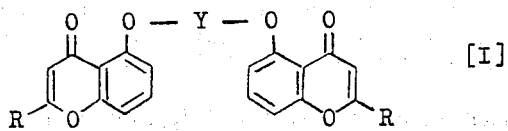

[I]

wherein R is aryl which may have one or more possible substituents, thienyl, furyl or pyridyl and Y is hydroxy(lower)alkylene, and the following general formula;

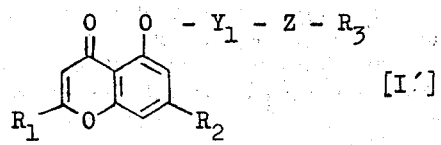

[I']

wherein $R_1$ is hydrogen, lower alkyl or aryl which may have one or more possible substituents or heterocyclic group, $R_2$ is hydrogen or lower alkoxy, $Y_1$ is lower alkylene or hydroxy(lower)alkylene, Z is oxygen or sulfur and $R_3$ is hydrogen, lower alkyl or aryl which may have one or more possible substituents or ar(lower)alkyl.

It has been found that the chromone compounds of the formulae [I] and [I'] possess an anti-allergic activity, and may be useful in a therapeutic and precautionary treatment for asthma.

It is an object of the present invention to provide new chromone compounds of the formulae [I] and [I']. These new chromone compounds possess anti-allergic activity and are useful as a therapeutic and precautionary treatment for asthma. Furthermore, there may be provided a pharmaceutical composition comprising, as an active ingredient, new chromone coompounds of the formulae [I] and/or [I'] and pharmaceutically acceptable carriers, as therapeutic and precautionary agents for asthma.

According to a still further feature of the invention, there are provided processes for preparing new chromone compounds of the formulae [I] and [I']. Other objects and advantageous features of the invention will be apparent to those conversant with the art to which the present invention pertains from the subsequent decription.

The process of the present invention is illustrated in the following reaction schemes:

SCHEME I

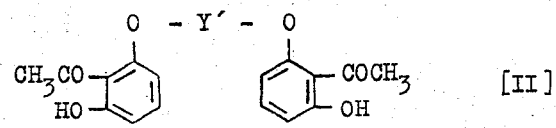

[II]

(i) R-COOH [III] or its reactive derivative (ii) Acid

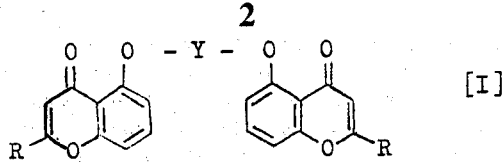

[I]

wherein Y' is hydroxy(lower)alkylene whose hydroxy group may be protected with possible protecting group and R and Y are each as defined above.

SCHEME II

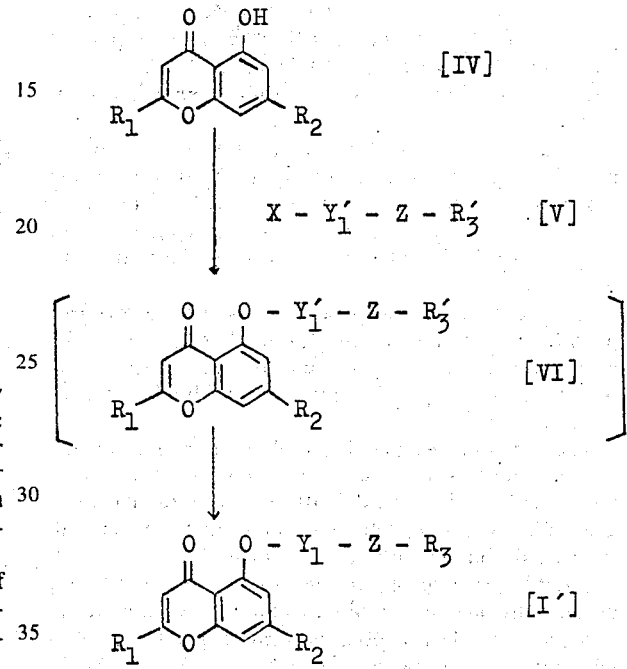

wherein X is acid residue, $Y'_1$ is lower alkylene or hydroxy(lower)alkylene whose hydroxy group may be protected with a protecting group, $R'_3$ is hydrogen, lower alkyl or aryl which may have one or more substituents or ar(lower)alkyl and $R_1$, $R_2$, $Y_1$, Z and $R_3$ are each as defined above, provided that when $R'_3$ is hydrogen, $-Z-R_3'$ may be protected with a protecting group.

Suitable lower alkyl moieties in the lower alkyl and the ar(lower)alkyl groups in the above formula, includes for example a monovalent aliphatic hydrocarbon having 1 to 6 carbon atoms, such as methyl, ethyl, propyl, isopropyl, butyl, isobutyl, tertiary-butyl, pentyl, hexyl, cyclohexyl and the like. Lower alkyl having 1 to 4 carbon atoms is preferred.

Suitable aryl moieties in the aryl and the ar(lower)alkyl groups in the above formulae, include for example a monovalent aromatic hydrocarbon of not more than 10 carbon atoms, such as phenyl, tolyl, naphthyl and the like. The aforementioned aryl group may have one or more suitable substituents, for example, lower alkoxy (e.g., methoxy, ethoxy, propoxy, butoxy, isopropoxy, isobutoxy, tertiary-butoxy, pentoxy, isopentoxy, hexyloxy, etc.), halogen (e.g., chlorine, bromine, iodine and fluorine), carboxy, esterified carboxy (e.g., methoxycarbonyl, ethoxycarbonyl, propoxycarbonyl, isopropoxycarbonyl, butoxycarbonyl, phenyloxycarbonyl, benzyloxycarbonyl, etc.), and the like.

Suitable lower alkylene moieties in the lower alkylene and the hydroxy(lower)alkylene groups in the above formulae, include for example by-valent aliphatic hydrocarbon having 1 to 6 carbon atoms, such as methylene, ethylene, methylethylene, propylene, butylene, ethylbutylene, pentylene, hexylene and the like. Lower alkylene having 1 to 4 carbon atoms is preferred.

Suitable lower alkoxy groups in the above formula, include for example lower alkoxy having 1 to 6 carbon atoms, such as methoxy, ethoxy, propoxy, isopropoxy, butoxy, isobutoxy, tertiary-butoxy, pentoxy, hexyloxy and the like. Lower alkoxy having 1 to 4 carbon atoms is preferred.

Suitable heterocyclic groups in the above formula, include for example, an unsaturated heteromonocyclic group containing one or more nitrogen, oxygen or sulfur atoms, (e.g., pyridyl, furyl, pyrimidinyl, ethienyl, etc.), and the like.

Suitable acid residues in the above formula, include for example acid residue from an acid, such as hydrochloric acid, sulfuric acid, hydrobromic acid, hydriodic acid, alkyl sulphate, toluenesulfonic acid, benzenesulfonic acid, dialkyl carbamate and the like.

Suitable possible protecting groups for the hydroxy group in the above formula, include for example, tetrahydropyranyl, dihydropyranyl, trimethylsilyl, triethylsilyl, tertiarybutyl, benzyl, acyl [e.g., alkoxycarbonyl such as methoxycarbonyl and ethoxycarbonyl, haloalkoxycarbonyl such as 2-trichloroethoxycarbonyl and 2-tribromoethoxycarbonyl, benzoyl, 2-(benzyloxycarbonyl)benzoyl, etc.], and the like.

Suitable possible protecting groups for the mercapto group in the above formula, include, for example, tetrahydropyranyl, dihydropyranyl, trimethylsilyl, triethylsilyl, tertiarybutyl, benzyl, p-methoxybenzyl, trityl, acyl [e.g., alkoxycarbonyl such as methoxycarbonyl and ethoxycarbonyl, haloalkyl such as 2-trichloroethoxycarbonyl and tribromoethoxycarbonyl, benzoyl, 2-(benzyloxycarbonyl)benzoyl, benzyloxycarbonyl, etc.], and the like.

The compound of the formula [I] can be prepared by reacting a compound of the formula [II] with a carboxylic acid of the formula [III] or its reactive derivative in the presence of a basic catalyst and then reacting the resultiing compound with an acid. The reaction may be carried out in an inert solvent.

One of the starting compound [II], 1,3-bis(3-hydroxy-2-acetylphenoxy)-2-hydroxypropane, can be prepared by the method described in Belgian Pat. No. 678,175. Other starting compounds [II] can be obtained in a similar manner.

Suitable reactive derivatives of the compound [III], include for example, the acid halide (e.g., acid chloride, the acid bromide, etc.), acid ester (e.g., methyl ester, ethyl ester, propyl ester, isopropyl ester, cyanomethyl ester, p-nitrophenyl ester, pentachlorophenyl ester, 2,4,5-trichlorophenyl ester, etc.), and the like.

Suitable basic catalysts for the reaction, include for example, alkali metal (e.g., lithium, sodium, potassium, etc.), metal alkoxide (e.g., lithium methoxide, lithium ethoxide, sodium methoxide, sodium ethoxide, sodium propoxide, sodium isopropoxide, potassium methoxide, potassium ethoxide, calcium methoxide, magnessium methoxide, aluminium methoxide, etc.), alkali metal amide (e.g., lithium amide, sodium amide, potassium amide, etc.), alkali metal hydride (e.g., lithium hydride, sodium hydride, potassium hydride, etc.), Grignard reagent (e.g., ethyl magnesium bromide, isopropyl magnesium bromide, diethylamino magnesium bromide, diisopropylaminomagnesium bromide, mesityl magnesium bromide, etc.), trityl alkali metal (e.g., trityllithium, tritylsodium tritylpotassium, etc.), and the like.

Suitable reaction solvents include for example, benzene, toluene, ether, alcohol, pyridine and other inert solvents. When the compound [II] or its reactive derivative is liquid, the reaction can be carried out even without the presence of the solvent. The reaction temperature is not particularly critical. It can range from room temperature to elevated temperature.

The resulting reaction product is then reacted with acid such as, for example, hydriodic acid, hydrochloric acid, hydrobromic acid, acetic acid, sulfuric acid and the like. The reaction can be carried out using two or more kinds of said acids at the same time and/or using a solvent such as alcohol (e.g., methanol, ethanol, etc.), and the like. The reaction temperature is not particularly critical the reaction is usually carried out under warming or heating.

When the compound [II] in which Y' is hydroxy(-lower)alkylene whose hydroxy group is protected with a protecting group is used, the protecting group is eliminated as the reaction with the acid proceeds.

The compound of the formula [I'] can be prepared by reacting a 5-hydroxychromone compound of the formula [IV] with a compound of the formula [V] and, when necessary, subjecting the resulting compound [VI] to elimination reaction to remove the protecting group.

5-Hydroxy-2-methylchromone, one of the starting compound [IV], can be prepared by the method described in the Chemical Abstracts, 52, 2002c (1956) and other compounds [IV] can be obtained in a similar manner.

The reaction of the compound [IV] with the compound [V] is preferably carried out in the presence of base, such as an alkali metal hydroxide (e.g., sodium hydroxide, potassium hydroxide, etc.), an alkali earth metal hydroxide (e.g., calcium hydroxide, magnesium hydroxide, etc.), an alkali metal carbonate (e.g., sodium carbonate, potassium carbonate, etc.), an alkali earth metal carbonate (e.g, calcium carbonate, magnesium carbonate, etc.), an alkali metal hydrogen carbonate (e.g., sodium hydrogen carbonate, potassium hydrogen carbonate, etc.), and the like. A mixture of more than two of the bases may be employed. To eliminate gas, such as hydrogen chloride, which is produced in the course of the reaction, it is advantageous to carry out the reaction by introduction of air or an inert gas such as nitrogen gas into the reaction vessel. This reaction may be carried out in a solvent, such as an organic solvent, e.g., dimethylformamide, dimethylsulfoxide, 1-methylpiperidinone, 1-methylpyrrolidinone, etc. and other inert organic solvents such as benzene, dioxane, n-hexane, acetone, etc. The reaction temperature is not particularly restrictive. The reaction is usually carried out under warming or heating.

When the resultant compound [VI] has a hydroxy or mercapto group which is protected by a protective group, the compound is subjected to elimination eaction so as to split off the protective group. The elimination reaction is carried out according to conventional methods such as decomposition with an acid, catalytic reduction, etc. The choice of the reaction depends on the nature of the protecting group to be split off. Decomposition with an acid is one of the most frequently used methods. It is preferred for splitting off protective groups such as tetrahydropyranyl, dihydropyranyl, trimethylsilyl, triethylsilyl, benzyloxycarbonyl, alkoxycarbonyl, 2-benzyloxycarbonyl, benzoyl, diphenylmethyl, trityl, t-butyl, etc. Preferred acids include hydrofluoric acid, hydrobromic acid, hydrochloric acid, formic acid, trifluoracetic acid, etc. The acid is selected dependending on the nature of the reaction. The decomposition reaction is frequently conducted in a hydrophilic organic solvent, water or a mixture of water and a hydrophilic organic solvent. Catalytic reduction is employed to split off protective groups such as benzyloxycarbonyl, benzyl, substituted benzyl, etc. Although other catalysts may be used palladium is preferred. Protective groups such as halogen-substituted alkoxycarbonyl and benzoyl may be split off by treatment with a heavy metal and with an alcoholate, respectively.

The chromone compound of the formulae [I] and [I'] exhibit an anti-allergic activity and can be used as a drug for treatment of asthma. The test results on some representative compounds of this invention are shown below.

1. Test method

Passive cutaneous anaphylaxis was produced by intravenous injection of an antigen (egg-albumin) to rats, each group consisting of 3 animals, sensitized with reagin-like rat antisera.* Evans blue dye was injected simultaneously with the antigen. The test compound (200 mg/kg) was given orally 2 hours before the administration of the antigen. The mean amount of dye in sensitized area of the test animals was compared with that of the control animals. Results were expressed as the percent inhibition. (* Preparation of reagin-like rat antisera against egg-albumin: Rats were injected with 1 ml of egg-albumin (1mg) plus $10^{10}$ killed B. pertussis (0.5 ml) mixture emulsified in 0.5 ml of complete Freund's adjuvant into the footpads. After 9 – 12 days, the serum was obtained and stored at −35°C.)

2. Test result

| Compound | Amount of Dye (Γ) | Inhibition (%) |
|---|---|---|
| 1,3-Bis(2-phenylchromon-5-yloxy)-2-hydroxypropane | 1.1 | 81.4 |
| 1,3-Bis[2-(2-furyl)chromon-5-yloxy]-2-hydroxypropane | 2.6 | 55.9 |
| 5-(2-Ethoxyethyloxy)-2 Phenylchromone | 2.7 | 54.3 |
| Control | 5.9 | |

Thus, the chromone compounds of the formulae [I] and [I'] are useful as an anti-allergic drug.

They can be administered by the conventional methods, the conventional types of unit dosages or with the conventional pharmaceutical carriers to produce an anti-allergic activity in human beings. Thus, they can be used in the form of pharmaceutical preparations, which contain the chromone compounds in admixture with a pharmaceutical organic or inorganic carrier material suitable for enteral or parenteral applications. Oral administration by the use of tablets, capsules or in liquid form such as suspensions, solutions or emulsions, or administration by injection are particularly advantageous. When formed into tablets, the conventional binding and disintegrating agents used in therapeutic unit dosages can be employed. Examples of binding agents that may be employed, include glucose, lactose, gum acacia, gelatin, mannitol, starch paste, magnesium trisilicate and talc. Examples of disintegrating agents that may be employed, include corn starch, keratin, colloidal silica and potato starch. When administered as liquids the conventional liquid carriers can be used.

The dosage or therapeutically effective quantity of the compounds [I] or [I'] for human beings can very over wide limits, for example from about 10 to 1000 milligrams/day for an adult. The upper limit is limited only by the dgree of effect desired and economic considerations. For oral administration from about 1 to 30 milligrams of the therapeutic agent per unit dosage is employed. For injection, from 1 to 10 mg of the active ingredient per unit dosage may be employed. Of course, the dosage of the active ingredient considerably can vary considerably since it depends on for example the age of the patient and the degree of therapeutic effect desired. The term pharmaceutical carrier is intended to include non-therapeutic materials which are conventionally used with unit dosage forms such as for example fillers, diluents, binders, lubricants, disintegrating agents and solvents. Of course, it is possible to administer the active ingredient, i.e. the pure compound, without the use of a pharmaceutical carrier.

It is desirable to administer the active ingredient with other therapeutic agents such as for example a bronchodilator.

The following examples are offered only for the purpose for purposes of illustrating the invention. They are not intended to limit the same.

EXAMPLE 1

Sodium hydride (3g) was gradually added, at room temperature and under stirring to a mixture of 1,3-bis(3-hydroxy-2-acetylphenoxy)-2-(2-tetrahydropyranyloxy)propane (3.0 g) and ethyl benzoate (25 cc) and the stirred mixture was heated for 15 hours at about 100°C. The reaction mixture was poured into ice-water and the aqueous solution was washed with ether, and then dil. hydrochloric acid was added to the same. Yellowish precipitates were extracted with ether, and the ether layer was washed with water, and dried. The solvent was then distilled off. The residue was dissolved in a mixture of methanol (50 cc) and conc. hydrochloric acid (5 cc), and the mixture so obtained was refluxed for 20 minutes and concentrated. The residue was dissolved in methanol, and the methanol solution was allowed to stand over night. Precipitates were collected by filtration and recrystallized from a mixed solvent of chloroform and methanol whereby colorless needles (0.7 g) of 1,3-bis(2-phenylchromon-5-yloxy)-2-hydroxypropane, m.p. 218° – 220°C were obtained.

Analysis: $C_{33}H_{24}O_7$ Calculated: C 74.43, H 4.54 Found: C 74.04, H 4.47.

The following compounds were obtained according to a manner similar to that of the preceding Example 1.

1. 1,3Bis[2-(3,4,5-trimethoxyphenyl)chromon-5-yloxy]-2-hydroxypropane tetrahydrate, m.p. 166° – 167°C. was obtained by reacting 1,3-bis(3-hydroxy-2- acetylphenoxy)-2-(2-tetrahydropyranyloxy)propane with ethyl 3,4,5-trimethoxybenzoate.

2. 1,3-Bis[2-(2-thienyl)chromon-5-yloxy]-2-hydroxypropane mono-hydrate, m.p. 187° – 188°C. was obtained by reacting 1,3-bis(3-hydroxy-2-acetylphenoxy)-2-(2-tetrahydropyranyloxy)propane with ethyl thiophene-2-carboxylate.

3. 1,3-Bis[2-(2-furyl)chromon-5-yloxy]-2-hydroxypropane hemihydrate, m.p. 224° – 226°C. was obtained by reacting 1,3-bis(3-hydroxy-2-acetylphenoxy)-2-(2-tetrahydropyranyloxy)propane with ethyl furan-2-carboxylate.

EXAMPLE 2

A solution of 1,3-bis(3-hydroxy-2-acetylphenoxy)-2-(2-tetrahydropyranyloxy)propane (2.2 g) and ethyl pyridine-4-carboxylate (1.6 g) in pyridine was added dropwise to a stirred suspension of sodium hydride (1.5 g) in dry pyridine (20 cc), and the stirred mixture was heated for 1 hour at about 100° – 110°C. The reaction mixture was poured into water. The aqueous solution was washed with ether twice, acidified with acetic acid and extracted with ether. The ether layer was washed in turn with water, an aqueous solution of sodium bicarbonate and water, and dried. The solvent was then distilled off. Methanol (50 cc) and hydrochloric acid (5 cc), were added to the residue and the resultant mixture was refluxed for 10 minutes. Precipitates were collected by filtration and suspended in water. The aqueous suspension was alkalized with an aqueous solution of sodium bicarbonate. Precipitates were collected by filtration and recrystallized from aqueous methanol whereby yellowish powder (0.8 g) of 1,3-bis[2-(4-pyridyl)chromon-5-yloxy]-2-hydroxypropane dihydrate, m.p. 165° – 167°C were obtained.

Analysis: $C_{31}H_{22}O_7N_2 \cdot 2H_2O$ Calculated: C 65.26, H 4.59, N 4.91 Found: C 65.04, H 4.65, N 4.86.

EXAMPLE 3

A mixture of 5-hydroxy-2-phenylchromone (9.5 g), 1-phenoxy-2-bromoethane (9.3 g), anhydrous potassium carbonate (6.6 g) and dimethylformamide (100 cc) was heated under stirring for 10 hours on a water-bath of 100°C. After the mixture cooled it was poured into ice-water and the aqueous solution was extracted with chloroform. The chloroform layer was washed with water and dried. The solvent was then distilled off. The residue was recrystallized from ethyl acetate whereby pale brown flakes (4.5 g) of 5-(2-phenoxyethoxy)-2-phenylchromone, m.p. 196° – 197°C were obtained.

Analysis: $C_{23}H_{18}O_4$ Calculated: C 77.08, H 5.06 Found: C 76.74, H 5.12.

The following compounds were obtained in accordance with a manner similar to that of the preceding Example 3.

1. Methyl 2-[2-(2-phenylchromon-5-yloxy)ethoxy]benzoate, m.p. 160° – 161°C. was obtained by reacting 5-hydroxy-2-phenylchromone with methyl 2-(2-bromoethoxy)benzoate.

2. 5-(2-Phenoxyethoxy)-2-(2-thienyl)chromone, m.p. 173° – 174.5°C. was obtained by reacting 5-hydroxy-2-(2-thienyl)chromone with 1-phenoxy-2-bromoethane.

3. 5-(2-Ethoxyethoxy)-2-(2-thienyl)chromone, m.p. 111° – 113°C. was obtained by reacting 5-hydroxy-2-(2-thienyl)-chromone with 1-ethoxy-2-bromoethane.

4. 5-(2-Phenylthioethoxy)-2-phenylchromone, m.p. 170° – 171°C. was obtained by reacting 5-hydroxy-2-phenylchromone with 1-phenylthio-2-bromoethane.

EXAMPLE 4

A mixture of 5-hydroxy-2-phenylchromone (730 mg), 1-phenoxy-2-bromoethane (700 mg), anhydrous potassium carbonate (460 mg) and dimethylformamide (7 cc) was refluxed under stirring for 1.5 hour while nitrogen gas was bubbled therein. After the mixture cooled, it was poured into ice-water. The resulting, and precipitates were collected by filtration, washed with water, dried and recrystallized from ethyl acetate whereby crystals of 5-(2-phenoxyethoxy)-2-phenylchromone, m.p. 196° – 197°C were obtained.

The following compounds were obtained according to a manner similar to that of the preceding Example 4.

1. 5-(2-Ethoxyethoxy)-2-phenylchromone, m.p. 94° – 96°C. was obtained by reacting 5-hydroxy-2-phenylchromone with 1-ethoxy-2-bromoethane.

2. 5-(2-Phenoxyethoxy)-2-methylchromone, m.p. 142° – 144°C. was obtained by reacting 5-hydroxy-2-methylchromone with 1-phenoxy-2-bromoethane.

EXAMPLE 5

A mixture of 5-hydroxy-2-phenylchromone (480 mg), 1-phenoxy-2-trimethylsilyloxy-3-chloropropane (1.0 g), anhydrous potassium carbonate (300 mg) and dimethylformamide (5 cc) was heated under stirring for 3 hours on an oil-bath of 120°C while nitrogen. Gas was bubbled therein. After the mixture cooled was poured into ice-water and the aqueous solution was extracted with chloroform. The chloroform layer was washed with water and the solvent was distilled off. The residue was dissolved in a mixture of methanol (15 cc) and conc. hydrochloric acid (3 cc), and the mixture was refluxed for 4 hours. The solvent was distilled off, and the residue was extracted with chloroform. The chloroform layer was washed in turn with water, an aqueous solution of sodium bicarbonate and water, and dried. The solvent was then distilled off. The residue was recrystallized from a mixed solvent of benzene and petroleum ether whereby crystals (300 mg) of 5-(3-phenoxy-2-hydroxypropoxy)-2-phenylchromone, m.p. 132° – 133°C were obtained.

Analysis: $C_{24}H_{20}O_5$ Calculated: C 74.21, H 5.19 Found: C 74.31, H 5.09.

The following compounds were obtained according to a manner similar to that of the preceding Example 5.

1. 5-(2-Hydroxyethoxy)-2-phenylchromone, m.p. 123.5° – 124.5°C. was obtained by reacting 5-hydroxy-2-phenylchromone with 1-(2-tetrahydropyranyloxy)-2-bromoethane.

2. 5-(2-hydroxyethoxy)-2-(2-thienyl)chromone, m.p. 160° – 161.5°C. was obtained by reacting 5-hydroxy-2-(2-thienyl)chromone with 1-(2-tetrahydropyranyloxy)-2-bromoethane.

3. 5-(3-Ethoxy-2-hydroxypropoxy)-2-phenylchromone, m.p. 85° – 86.5°C. was obtained by reacting 5-hydroxy-2-phenylchromone with 1-ethoxy-2-(2-tetrahydropyranyloxy)-3-chloropropane.

EXAMPLE 6

The following compounds were obtained according to a manner similar to those of the preceding Examples 3, 4 and 5.

1. 2-[2-(2-Phenylchromon-5-yloxy)ethoxy]benzoic acid, m.p. 184° – 185.5°C.

2. 7-Methoxy-5-(2-phenoxyethoxy)-2-phenylchromone, m.p. 156° – 157.5°C.

3. 5-(2-Ethylthioethoxy)-2-phenylchromone, m.p. 110° – 111°C.

4. 5-(2-Benzyloxyethoxy)-2-phenychromone, m.p. 102° – 103°C.

5. 5-(2-Ethoxyethoxy)-2-(3-pyridyl)chromone, m.p. 121° – 123°C.

6. 5-(2-Phenoxyethoxy)chromone, m.p. 100° – 101°C.

7. 5-(2-Ethoxyethoxy)chromone, b.p. (4mmHg) 183°C.

8. 5-(2-Ethoxyethoxy)-2-(3-chlorophenyl)chromone, m.p. 127° – 128.5°C.

EXAMPLE 7

A suitable formulation of tablets consists of:

|  | Grams |
|---|---|
| (1) 1,3-Bis(2-phenylchromon-5-yloxy)-2-hydroxypropane | 1 |
| (2) Lactose | 70 |
| (3) Starch | 5 |
| (4) Magnesium stearate | 2 |

There are produced 100 tablets each containing 10 mg of the active ingredient.

EXAMPLE 8

A suitable formulation of tablets consists of:

| (1) 5-(2-Ethoxyethoxy)-2-phenylchromone | 2 |
|---|---|
| (2) Mannitol | 90 |
| (3) Starch | 6 |
| (4) Magnesium stearate | 2 |

There are produced 100 tablets each containing 20 mg of the active ingredient.

What is claimed is:

1. A chromone compound selected from the group consisting of

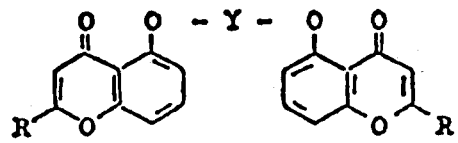

[I]

and

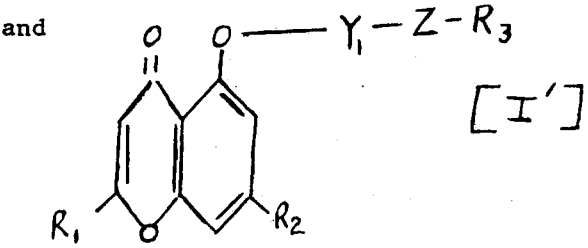

[I']

wherein
R is aryl or substituted aryl,
Y is hydroxy (lower) alkylene,
$R_1$ is hydrogen, lower alkyl, aryl, or substituted aryl,
$R_2$ is hydrogen or lower alkoxy,
$Y_1$ is lower alkylene or hydroxy (lower) alkylene,
$R_3$ is hydrogen, lower alkyl, aryl, substituted aryl or ar (lower) alkyl,
Z is oxygen or sulfur
said aryl and said ar each constituting a monovalent, aromatic hydrocarbon having up to 10 carbon atoms, said substituted aryl being aryl substituted by 1 or more of lower alkoxy, halogen, carboxy, lower alkoxy carbonyl, ar (lower) alkoxy carbonyl, and aryloxy carbonyl.

2. The compound according to claim 1 in which R is phenyl.

3. The compound according to claim 1 in which R is 3,4,5-trimethoxyphenyl.

4. A compound according to claim 1 having the formula

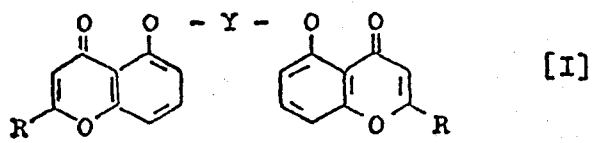

[I]

5. A compound according to claim 1 wherein R is aryl substituted with lower alkoxy.

6. A chromone compound of claim 1 having the formula:

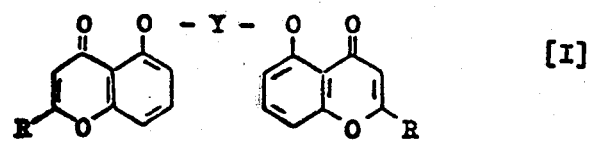

[I]

wherein R is aryl and Y is hydroxy(lower)alkylene.

7. The compound according to claim 1 having the formula [I'].

8. The compound according to claim 7 in which $R_1$ is hydrogen, methyl, phenyl, or chlorophenyl, $R_2$ is hydrogen or methoxy, $Y_1$ is ethylene or hydroxypropylene, Z is oxygen or sulfur and $R_3$ is hydrogen, ethyl, phenyl, carboxyphenyl, methoxycarbonyl-phenyl or benzyl.

* * * * *